United States Patent [19]

Rappoport

[11] Patent Number: 5,927,299
[45] Date of Patent: Jul. 27, 1999

[54] HYGIENIC TOOTH CLEANSING DEVICE

[76] Inventor: Victor Rappoport, P.O. Box 1297, Studio City, Calif. 91604

[21] Appl. No.: 09/025,743

[22] Filed: Feb. 18, 1998

Related U.S. Application Data

[60] Provisional application No. 60/055,635, Aug. 18, 1997.
[51] Int. Cl.[6] .................................................. A61C 15/00
[52] U.S. Cl. ............................................ 132/321; 132/329
[58] Field of Search ................................... 132/321, 329; 433/141, 215, 216, 229

[56] References Cited

U.S. PATENT DOCUMENTS

| | | | |
|---|---|---|---|
| 2,762,501 | 9/1956 | Cameron | 132/329 |
| 3,771,537 | 11/1973 | Schole | 433/142 |
| 3,809,103 | 5/1974 | Bender | 132/329 |
| 4,270,556 | 6/1981 | McAllister | 132/321 |
| 5,769,103 | 6/1998 | Turjak | 132/329 |

FOREIGN PATENT DOCUMENTS

| | | | |
|---|---|---|---|
| 0012228 | 11/1979 | European Pat. Off. | 132/329 |
| 9305726 | 4/1993 | WIPO | 132/321 |

*Primary Examiner*—John J. Wilson
*Attorney, Agent, or Firm*—Roger A. Marrs

[57] ABSTRACT

A dental hygienic teeth and gum cleansing device having an elongated metal foil or filament member adapted to be drawn between the adjacent teeth of the user for removal of and cleansing of the dental area. The metal foil may be rounded at its opposite ends and may include a thickened handle at one end. A selected edge of the metal foil may include alternate ridges and grooves for dislodgment of and collection of oral debris and foreign matter. The thickness of the metal foil member may be at least 0.002 inches with the width of the member being at least 0.25 inches.

1 Claim, 1 Drawing Sheet

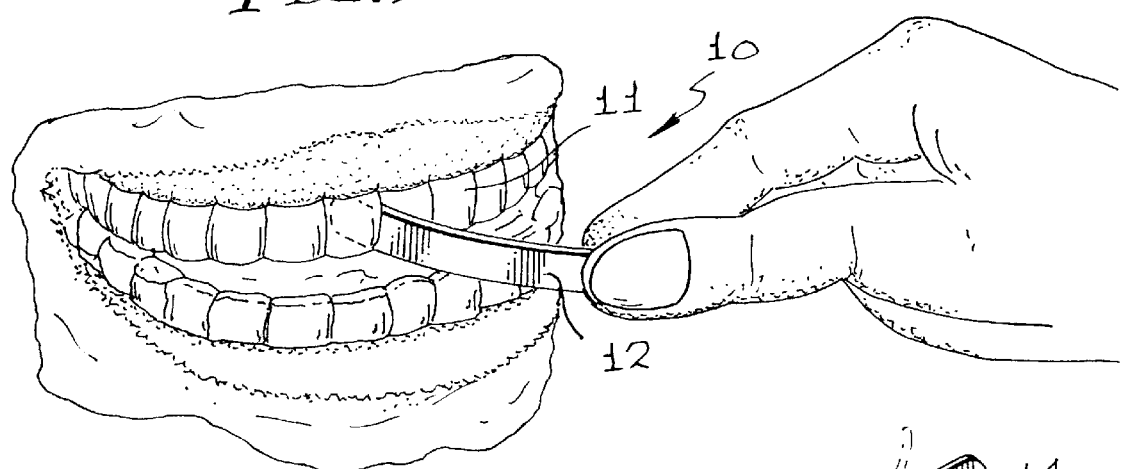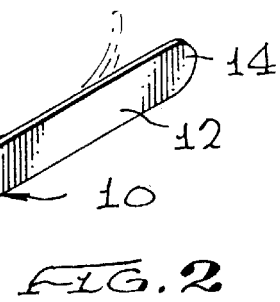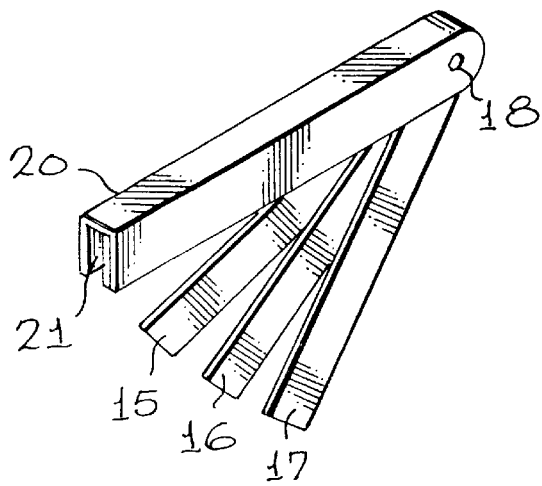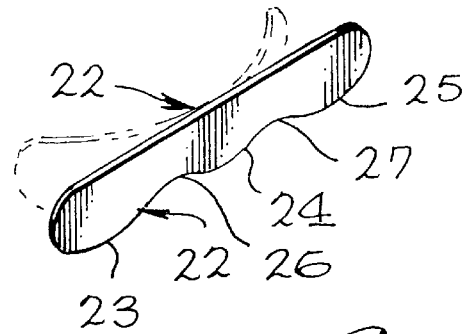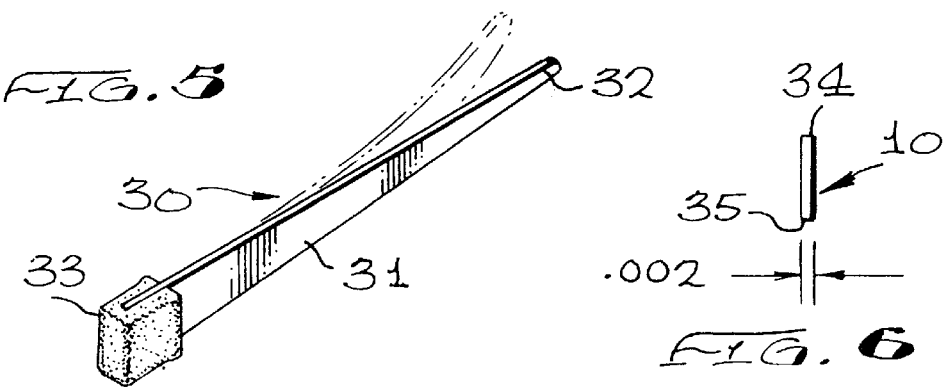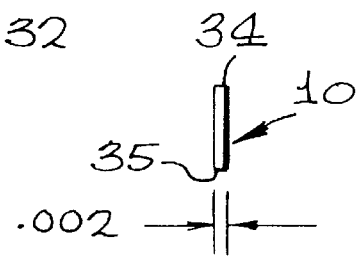

HYGIENIC TOOTH CLEANSING DEVICE

This application claims the benefit of U.S. Provisional Application No. 60/055,635, filed Aug. 18, 1997.

BACKGROUND OF THE INVENTION

1. Field of the Invention

The present invention relates to the field of medical dental hygienics, and more particularly to a novel flexible strip employed for cleansing the debris from areas adjacent to teeth and gums.

2. Brief Description of the Prior Art

In the past, it has been the conventional practice to cleanse one's teeth by employing waxed filaments such as strings or threads which are drawn between adjacent teeth so as to engage and dislodge debris. Other means have been employed which include conventional toothpicks which are rigid and include pointed ends which are forcibly urged between adjacent teeth to dislodge debris. Still more recent devices have been employed which comprise bow-shaped holders for threads or the like which are then drawn between adjacent teeth while the user grasps onto the holder.

Difficulties and problems have been encountered when using such conventional dental hygienic devices which stem largely from the fact that not all debris is dislodged and there is no means for collecting debris once dislodgement has taken place. Furthermore, although the devices have been useful in cleansing or removing foreign matter and debris from the tooth and gum area, there is not advantage through gum massage for using the device. Gum massaging devices generally include a rigid handle on which a soft tip or material is placed so that a rubbing action can occur against the gum. Also, it is difficult for a user to hold conventional toothpicks, waxed threads or the like and by employing holders, it is required that the holder be placed inside the mouth which may be unsanitary and certainly uncomfortable.

Therefore, a long-standing need has existed to provide a novel tooth debris or foreign matter removal device which may be conveniently held by the user and which not only performs a cleansing procedure but aids in gum massage as well.

SUMMARY OF THE INVENTION

Accordingly, the above problems and difficulties are avoided by the present invention which provides a novel ultra-thin filament which is grasped by the user and is drawn in the space between adjacent teeth so as to engage and dislodge foreign matter and debris from the gum line and between the teeth. The filament includes opposite ends that may be grasped by the fingers of the user and may include a series of raised portions followed by grooves or cavities into which the debris can be collected as the filament is reciprocally moved between the teeth. Also, a handle or grasping means may be placed on one end of the filament for readily holding the filament between the fingers of the user and, if desired, a tapered end can be provided for use as a toothpick projection. A case may be provided having a cavity for pivotally receiving one or more filaments of different thickness so that a variety of tooth spaces between adjacent teeth can be accommodated. In one form, one end of the filament may be provided with a hole to receive a pivot pin when attached to one end of a case.

It is to be understood that the term filament herein is meant to include a flexible member having a thickness of at least 0.002 inches and which includes a predetermined length and predetermined width so as to accommodate the grasping of the member by the user. The term filament is not intended to include threads, wooden rods or shafts or paper strips.

Therefore, it is among the primary objects of the present invention to provide a metal filament or foil member which is flexible and which includes upper and lower edges for debris and removal purposes when used to cleanse a person's mouth between adjacent teeth and the gums.

Another object of the present invention is to provide a novel dental cleansing device composed of a metal foil or filament which is drawn between adjacent teeth of the user and which may be hand held so that the gums are massaged simultaneously with teeth cleansing.

Still another object of the present invention is to provide a novel metal filament or foil member having means for dislodging debris from the gum line of the user and which may collect the debris for easy removal from the user's mouth.

A further object of the present invention is to provide a novel dental cleansing device which includes a plurality of different thickness metal foils that are carried in a case so that the foils may be readily selected by the user and pivoted from a storage position in the case for user to cleanse the user's teeth and gums.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a perspective view showing the novel flexible metal foil or filament of the present invention used to cleanse debris from the space between adjacent teeth;

FIG. 2 is a perspective view of the flexible metal foil or filament member shown in FIG. 1;

FIG. 3 is a perspective view showing a plurality of flexible metal filaments held in a common case preparatory for use;

FIG. 4 is a perspective view of another version of the present invention illustrating means for dislodging debris and collecting the debris for removal from the mouth;

FIG. 5 is a perspective view of another version illustrating a device that may be used as a toothpick in addition to cleansing between adjacent teeth; and FIG. 6 is an enlarged view showing a typical dimension for the thickness of the flexible metal foil not to be less than 0.002 inches.

DESCRIPTION OF THE PREFERRED EMBODIMENT

Referring to FIG. 1, the novel dental cleansing appliance or device incorporating the present invention is illustrated in the general direction of arrow 10 and is illustrated in connection with removing debris from between the teeth 11 of the user. The appliance or device 10 takes the form of a flat steel blade or flexible member 12 which is elongated and has at least a thickness of 0.002 inches. The flat steel blade is flexible and is grasped between the fingers of the user at one end and then inserted between adjacent teeth and then drawn through the space between the teeth in order to remove any debris or foreign matter.

Referring to FIG. 2, the flat metal blade 12 is illustrated as being flexible in broken lines and the blade 12 is elongated having opposite ends 13 and 14 respectively. The opposite ends are rounded in order to avoid sharp points which may cause injury. Preferably, the composition of the metal blade is composed of steel so that it can be made thin and flexible and so that it can be used over and over without losing its effectiveness. Spring steel is preferred so that the appliance will return to the solid line position, as shown in FIG. 2, although it may be bent or twisted to accommodate the use to which the user places the appliance.

In FIG. 3, it can be seen that the teeth cleaner or appliance of the present invention may comprise multiple steel blades, such as identified by numerals 15, 16 and 17, and wherein each of the respective steel blades are pivotally mounted via a pivot 18 carried on one end of a case 20. The case 20 includes an open cavity or storage compartment 21 into which the multiple blades 15–17 may be stored when not in use. The respective steel blades 15–17 are of different thicknesses so that the user may select a particular thickness to accommodate the space between his teeth intended to be cleaned. In order to mount the multiple blades to the case 20, it is preferred that one end of each of the blades includes a hole or opening in order to receive the pivot 18 for mounting purposes.

Referring now in detail to FIG. 4, another embodiment of the invention is illustrated in the general direction of arrow 22 which is similar to the embodiment 10 shown in FIG. 1. However, the device or appliance 22 includes at least one edge marginal region which comprises a series of raised nodes represented by numerals 23, 24 and 25 that are separated by deep pockets, cavities or notches, as indicated by numerals 26 and 27. When the steel blade 22 is drawn between the teeth of the user, debris and other foreign matter is dislodged by the nodes 23–25 inclusive and the debris is collected in the respective notches 26 or 27. Therefore, the embodiment shown in FIG. 4 is useful in not only dislodging foreign matter from between the teeth or adjacent to the gums but is useful in physically collecting and removing the debris from the user's mouth. Again, the flexibility of the blade is shown in broken lines.

Referring now in detail to FIG. 5, another version of the invention is illustrated in the general direction of arrow 30 wherein the embodiment includes a blade 31 having a taper terminating in an end 32 of reduced width so as to be used as a toothpick, if needed. The opposite end of the blade 31 includes a finger-grasping handle or cushion, identified by numeral 33. Again, flexibility is illustrated in broken lines.

FIG. 6 illustrates that the thickness of the blade for blades 12, 22 or 31 is at least 0.002 inches. The blade includes an upper edge marginal region 34 and a lower edge marginal region 35 that may slightly engage with the gums of the user as the blade is being drawn in the space between adjacent teeth so that the gum is massaged. Preferably, the edges defining the edge marginal regions about the steel blade are not sharp and may be rounded so as to ensure that the user will not cut or injure the gum. Also, it is to be understood that the nodes and notches as shown in FIG. 4 may be incorporated into the blade 12 of FIG. 2 and the blade 31 shown in FIG. 5 without departing from the present invention. By inserting the flat steel blade or member in the space between adjacent teeth, offending substances, debris or other foreign matter can be removed. In actual practice, the inventive device will even remove dental floss that has been broken off and is stuck between the teeth, such as may occur during a preceding flossing procedure.

The steel blade may easily be cleaned after use by washing or by periodic washing with a medical liquid such as alcohol or the like.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A hygienic tooth cleaning device comprising:

an elongated metal member having opposite ends separated by a midsection;

said member having an upper edge marginal region and a lower edge marginal region to be employed in dislodging debris from between the teeth of the user;

said member having a critical thickness of no more than 0.002 inch whereby said member is flexible and adapted to be flexed about said midsection;

said member includes an overall length substantially of greater dimension than its width;

at least one end of said member is rounded and its opposite end constitutes a finger-gripping end;

said finger-gripping end constitutes a handle grip;

a case having an internal storage compartment;

a plurality of said elongated members pivotally carried on said case movable into and out of said storage compartment;

a selected one of said upper and lower edge marginal regions of each of said elongated members includes a scalloped edge of alternate rounded regions separated by rounded grooves for collection of removed debris;

each of said members is tapered from said handle grip to its opposite end terminating in a reduced rounded tip;

each of said elongated members is a metal foil and is intended to be disposed of after use; and said upper edge marginal region is linear across said central area and said lower edge marginal region includes a scalloped edge between said member opposite ends.

* * * * *